(12) United States Patent
Chen

(10) Patent No.: US 8,657,739 B2
(45) Date of Patent: Feb. 25, 2014

(54) ENDOSCOPIC IMAGE PICKUP DEVICE WITH MULTIPLE ILLUMINATION DIRECTIONS

(75) Inventor: Sung-Nan Chen, Taoyuan County (TW)

(73) Assignee: Medical Intubation Technology Corporation, Taoyuan County (TW)

( * ) Notice: Subject to any disclaimer, the term of this patent is extended or adjusted under 35 U.S.C. 154(b) by 140 days.

(21) Appl. No.: 13/214,522

(22) Filed: Aug. 22, 2011

(65) Prior Publication Data

US 2012/0184811 A1 Jul. 19, 2012

(30) Foreign Application Priority Data

Jan. 18, 2011 (TW) .............................. 100101814 A

(51) Int. Cl.
*A61B 1/06* (2006.01)
*A61B 1/07* (2006.01)
(52) U.S. Cl.
USPC ........... 600/170; 600/173; 600/175; 600/178; 600/179; 600/182
(58) Field of Classification Search
CPC .................................................... A61B 1/0623
USPC ......... 600/178, 179, 182, 170, 171, 173, 175, 600/177
See application file for complete search history.

(56) References Cited

U.S. PATENT DOCUMENTS 4,697,577 A * 10/1987 Forkner ......................... 600/173
5,547,455 A * 8/1996 McKenna et al. ............. 600/113
5,700,236 A * 12/1997 Sauer et al. .................... 600/175
6,248,060 B1 * 6/2001 Buess et al. .................... 600/182
6,251,068 B1 * 6/2001 Akiba et al. ................... 600/182
6,569,088 B2 * 5/2003 Koshikawa .................... 600/177
6,735,367 B2 * 5/2004 Sanso ............................ 385/117
7,585,274 B2 * 9/2009 Homma ......................... 600/160
7,801,584 B2 * 9/2010 Iddan et al. .................... 600/407
8,123,680 B2 * 2/2012 Kato et al. ..................... 600/177
8,202,214 B2 * 6/2012 Doguchi et al. ............... 600/168
2001/0003142 A1 * 6/2001 Koshikawa .................... 600/177
2002/0128538 A1 * 9/2002 Thompson .................... 600/121
2004/0122290 A1 * 6/2004 Irion et al. ..................... 600/171
2004/0225189 A1 * 11/2004 Kimoto et al. ................ 600/160
2005/0049462 A1 * 3/2005 Kanazawa ..................... 600/170
2006/0217592 A1 * 9/2006 Miyagi et al. ................. 600/130

(Continued)

FOREIGN PATENT DOCUMENTS

JP 10288742 A * 10/1998 ............. G02B 23/26

*Primary Examiner* — John P Leubecker
(74) *Attorney, Agent, or Firm* — Muncy, Geissler, Olds & Lowe, P.C.

(57) ABSTRACT

An endoscopic image pickup device includes a tubing, an image pickup module consisting of a lens and an image sensor and installed in one end of the tubing, a first light source installed in the same end of the tubing relative to the image pickup module and having an illumination range directly intersected with the image pickup range of the image pickup module, a second light source installed in the tubing and having an illumination range deviated from the illumination range of the first light source a predetermined angle and intersected with the illumination range of the first light source directly or indirectly, and a light source control means adapted for controlling on and/or off of said first light source and/or said second light source. Subject to the design that the illumination direction of the second light source is deviated from that of the first light source, the invention provides an extra illumination range, enhancing image clarity.

10 Claims, 5 Drawing Sheets

(56) References Cited

U.S. PATENT DOCUMENTS

| | | | |
|---|---|---|---|
| 2007/0038031 A1* | 2/2007 | Miyagi et al. | 600/182 |
| 2007/0055106 A1* | 3/2007 | Moriyama | 600/178 |
| 2007/0073109 A1* | 3/2007 | Irion | 600/179 |
| 2008/0208006 A1* | 8/2008 | Farr | 600/178 |
| 2009/0069633 A1* | 3/2009 | Orihara et al. | 600/163 |
| 2010/0272318 A1* | 10/2010 | Cabiri et al. | 382/106 |
| 2010/0324373 A1* | 12/2010 | Lei et al. | 600/176 |
| 2011/0196200 A1* | 8/2011 | Glozman et al. | 600/109 |

* cited by examiner

ENDOSCOPIC IMAGE PICKUP DEVICE WITH MULTIPLE ILLUMINATION DIRECTIONS

BACKGROUND OF THE INVENTION

1. Field of the Invention

The present invention relates to endoscope technology and more particularly, to an endoscopic image pickup device that provides multiple illumination directions.

2. Description of the Related Art

A regular endoscope, either for industrial or medical application, generally uses an image pickup device (a combination of a tube, a lens and a light source) in the front end of a tubing for illumination and image pickup. When picking up images, the light source provides illumination, and the lens picks up the images. When inserting the tubing into the inside of an object to the target to be examined, the light source illuminates the target, enabling the lens to pick up the images of the target and to transfer the images to a display screen for display. Thus, the user can observe the images displayed on the display screen to check the target that is not directly visible with the bare eyes.

In the aforesaid conventional endoscope, the illumination direction of the light source in the front end of the tubing is parallel to the image pickup direction of the lens. Therefore, under normal conditions, the area illuminated by the light source covers the image pickup range of the lens, enabling the lens to pick up images effectively. However, if the lens is a wide-angle lens, the image pickup range will be greater than the illumination range of the light source. In this case, the center area of the fetched image will be relatively brighter than the border area. Thus, the image picked up from a dark area may be no clear.

Further, when the image pickup device of the aforesaid endoscope is operated to pickup side images, a side view attachment may be used. A side view attachment for this purpose generally comprises a reflector and a transparent window located on one lateral side. The reflector reflects incident light passing through the transparent window onto the lens for image pickup. However, as the illumination direction of the light source in the endoscope is parallel to the image pickup direction of the lens, the light emitted by the light source falls directly upon the reflector and then reflector reflects the light onto the target at first, and the light reflected by the target will then be reflected by the reflector onto the image pickup lens. Under this operation manner, the coating quality of the reflector must be excellent to assure image clarity. Further, the reflective surface of the reflector must be constantly kept clean, any contamination of the reflective surface of the reflector will cause scattering of light, affecting picture quality.

SUMMARY OF THE INVENTION

The present invention has been accomplished under the circumstances in view. It is the main object of the present invention to provide an endoscopic image pickup device with multiple illumination directions, which, in addition to the function of using a first light source to give off light for illumination and image pickup like the conventional illumination method, provides an extra second light source to give an extra illumination range beyond the radiation direction of the first light source, enhancing image clarity.

To achieve this and other objects of the present invention, an endoscopic image pickup device comprises a tubing, an image pickup module consisting of a lens and an image sensor and installed in one end of the tubing, a first light source installed in the same end of the tubing relative to the image pickup module and having an illumination range directly intersected with the image pickup range of the image pickup module, a second light source installed in the tubing and having an illumination range deviated from the illumination range of the first light source a predetermined angle and intersected with the illumination range of the first light source directly or indirectly, and a light source control means adapted for controlling on and/or off of said first light source and/or said second light source. Subject to the design that the illumination direction of the second light source is deviated from that of the first light source, the invention provides an extra illumination range, enhancing image clarity.

Other advantages and features of the present invention will be fully understood by reference to the following specification in conjunction with the accompanying drawings, in which like reference signs denote like components of structure.

DETAILED DESCRIPTION OF THE INVENTION

Figure 1:
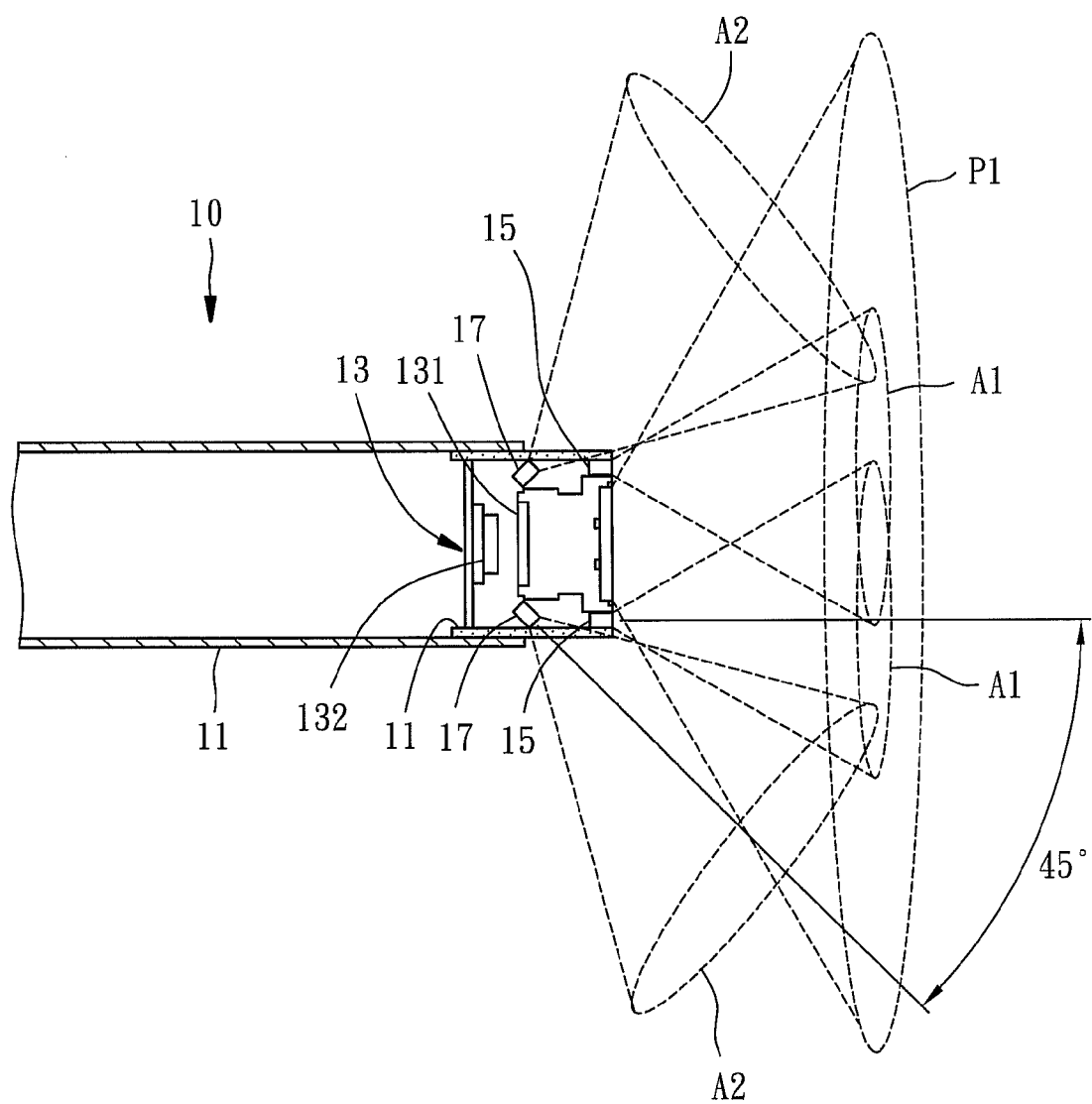
FIG. 1 is a schematic sectional view of an endoscopic image pickup device in accordance with a first embodiment of the present invention.
Figure 2:
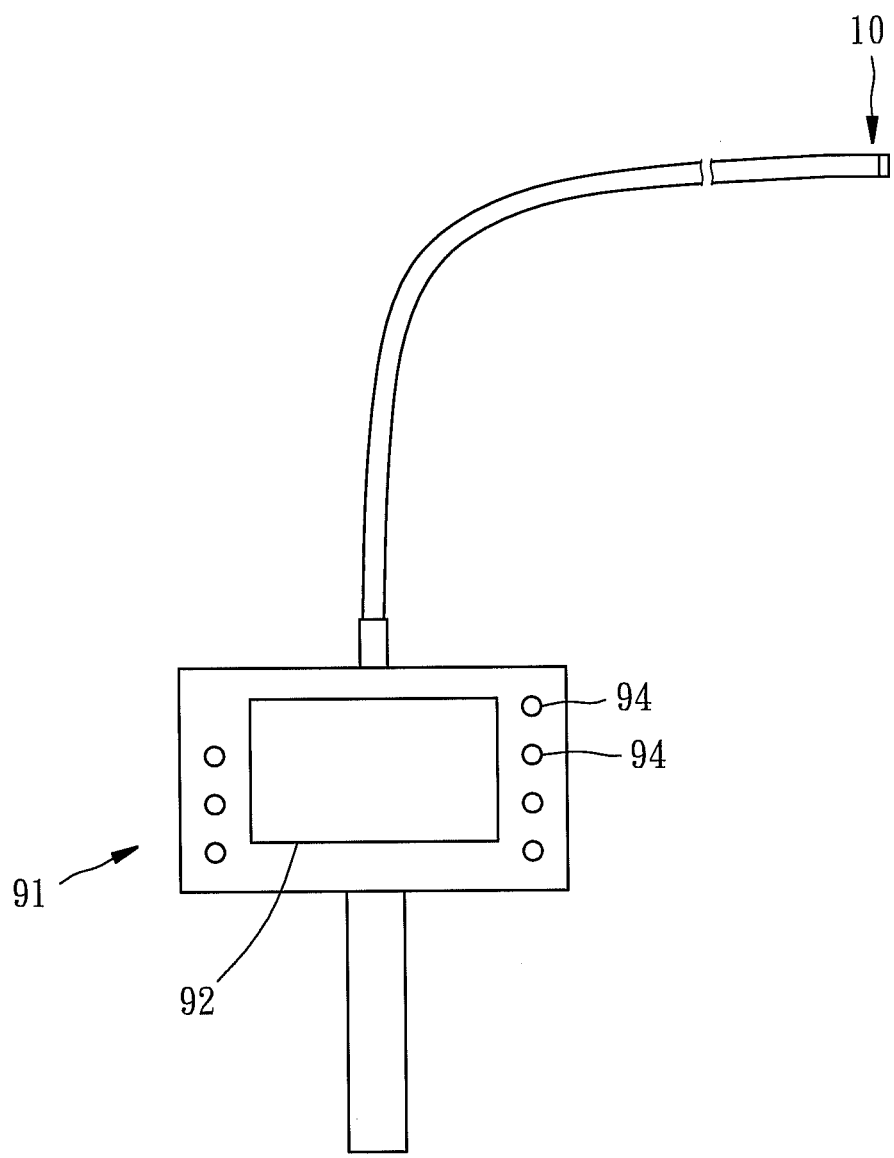
FIG. 2 is a schematic elevational view of the first embodiment of the present invention, illustrating the endoscopic image pickup device connected to an endoscope.

Referring to FIGS. 1 and 2, an endoscopic image pickup device 10 in accordance with a first embodiment of the present invention is shown comprising a tubing 11, an image pickup module 13, a first light source 15 and a second light source 17.

The tubing 11 (according to this embodiment, it is formed of two tube members connected in series) has its rear end connected to an operating device 91. The operating device 91 is equipped with a display screen 92 and a set of buttons 94, and electrically connected with the image pickup module 13, the first light source 15 and the second light source 17. Further, the front end of the tubing 11 is partially transparent. As the electrical connection arrangement of the operating device 91 is of the known art and not within the scope of the invention, no further detailed description in this regard is necessary.

The image pickup module 13 consists of a lens 131 and an image sensor 132, and is arranged in the front end of the tubing 11.

The first light source 15 consists of a plurality of light-emitting components (not shown), and is mounted with the image pickup module 13 in the front end of the tubing 11. The illumination range A1 of the first light source 15 intersects the image pickup range P1 of the image pickup module 13. According to this embodiment, the illumination direction of the first light source 15 extends in a parallel manner relative to the image pickup direction of the image pickup module 13. In other embodiments, due to installation tolerance, the illumination direction of the first light source 15 and the image pickup direction of the image pickup module 13 may be not kept in parallel. An angle difference within a limited range still allows intersection between the illumination range A1 of the first light source 15 and the image pickup range P1 of the image pickup module 13. This case is substantially similar to the embodiment where the illumination direction and the image pickup direction are kept in parallel, and therefore no further detailed description is necessary.

The second light source 17 consists of a plurality of light-emitting components (not shown), and is mounted in the tubing 11 behind the first light source 15 corresponding to the transparent part of the tubing 11. The illumination direction of the second light source 17 deviates from the illumination direction of the first light source 17 a predetermined angle (greater than) 30°, for example, 45°. Further, the illumination range A2 of the second light source 17 intersects the illumination range A1 of the first light source 15 directly.

In this embodiment, the number of the light-emitting components of the first and second light sources is not a limitation. The number of the light-emitting components is simply selected to match with the application. In other embodiments, the first and second light sources can be respectively formed of one single light-emitting component. Further, the first light source 15 and the second light source 17 can be configured to have the same wavelength or different wavelengths.

The operation of the endoscopic image pickup device 10 in accordance with the first embodiment of the present invention will be outlined hereinafter.

Referring to FIG. 1 again, during operation, the first light source 15 and the second light source 17 are controlled to emit light. At this time, the illumination range A1 of the first light source 15 directly intersects the image pickup range P1 of the image pickup module 13, but is relatively smaller than the image pickup range P1 of the image pickup module 13; the illumination range A2 of the second light source 17 directly intersects the illumination range A1 of the first light source 15, but is relatively smaller than the illumination range A1 of the first light source 15; the illumination direction of the second light source 17 deviates from the illumination direction of the first light source 17 at 45° angle. Thus, the second light source 17 provides an extra illumination range A2, covering an area within the image pickup range P1 of the image pickup module 13 where the illumination of the first light source 15 cannot reach.

Figure 3:
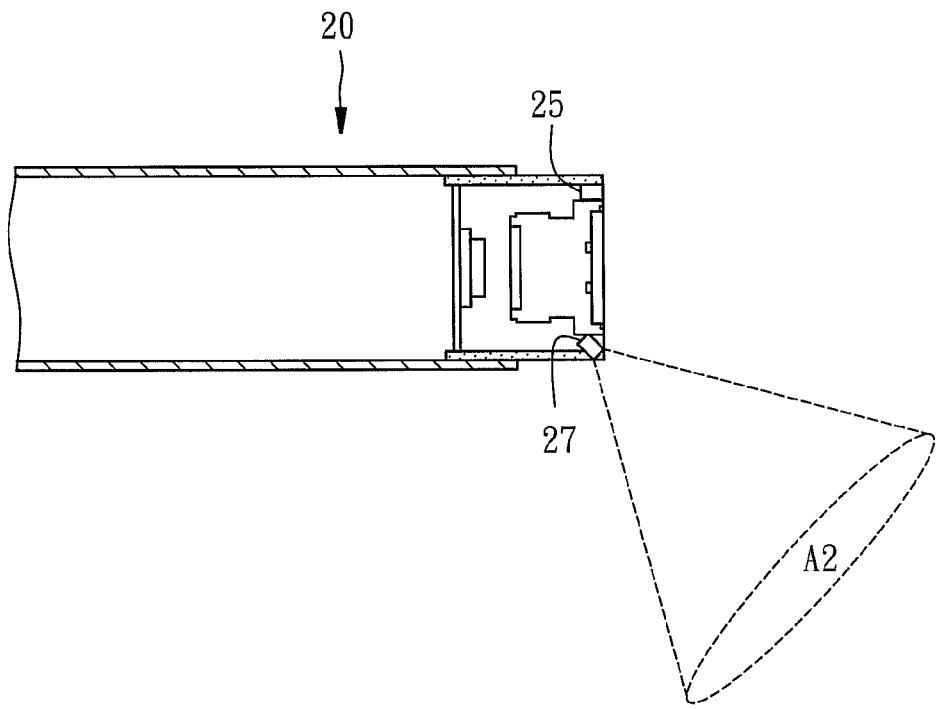
FIG. 3 is a schematic sectional view of an endoscopic image pickup device in accordance with a second embodiment of the present invention.

FIG. 3 illustrates an endoscopic image pickup device 20 in accordance with a second embodiment of the present invention. This second embodiment is substantially similar to the aforesaid first embodiment with the exception that the second light source 27 is mounted in the front end of the tubing; the first light source 25 and the second light source 27 each consist of one single light-emitting component. It is to be understood that the single light-emitting component arrangement of the first and second light sources according to this second embodiment is simply to match with the application but not intended for use as a limitation.

During operation of this second embodiment, the second light source 27 provides an extra illumination range A2 to improve image clarity in this illumination range.

The other structural details and the effects of this second embodiment are substantially same as the aforesaid first embodiment. Therefore, no further detailed description in this regard is necessary.

Figure 4:
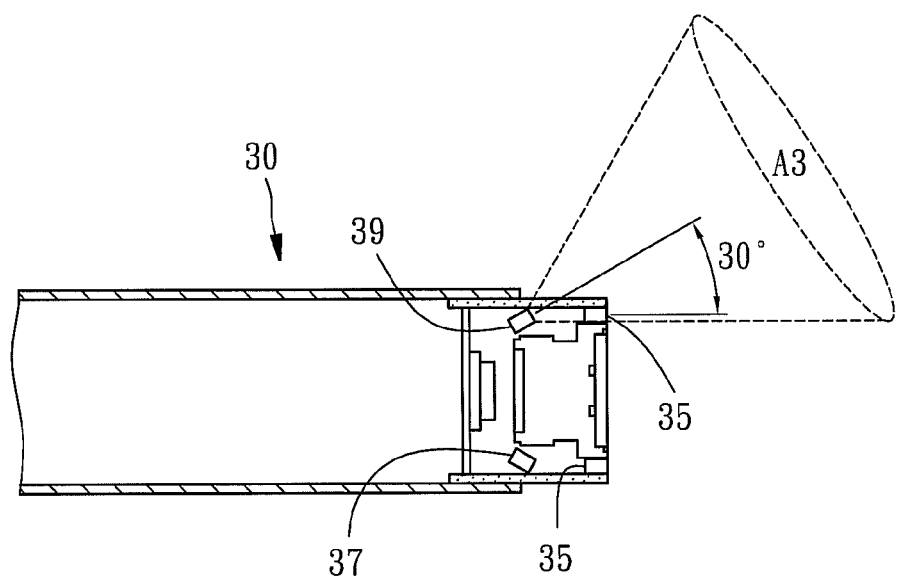
FIG. 4 is a schematic sectional view of an endoscopic image pickup device in accordance with a third embodiment of the present invention.

FIG. 4 illustrates an endoscopic image pickup device 30 in accordance with a third embodiment of the present invention. This third embodiment is substantially similar to the aforesaid first embodiment with the exception that this third embodiment further comprises a third light source 39. The illumination direction of the third light source 39 deviates from the illumination direction of the first light source 35 a predetermined first angle and also deviates from the illumination direction of the second light source 37 a predetermined second angle. According to this third embodiment, the angle of deviation between the illumination direction of the third light source 39 and the illumination direction of the first light source 35 is 30°.

The first light source 35 consists of a plurality of light-emitting components. The second and third light sources 37; 39 respectively consist of one single light-emitting component. It is to be understood that the design of single or multiple light-emitting components of the light sources is simply selected to match with the application but not intended for use as a limitation.

During operation of this third embodiment, the third light source provides an extra illumination range A3, improving image clarity in the illuminated area.

The other structural details and the effects of this third embodiment are substantially same as the aforesaid first embodiment. Therefore, no further detailed description in this regard is necessary.

Figure 5:
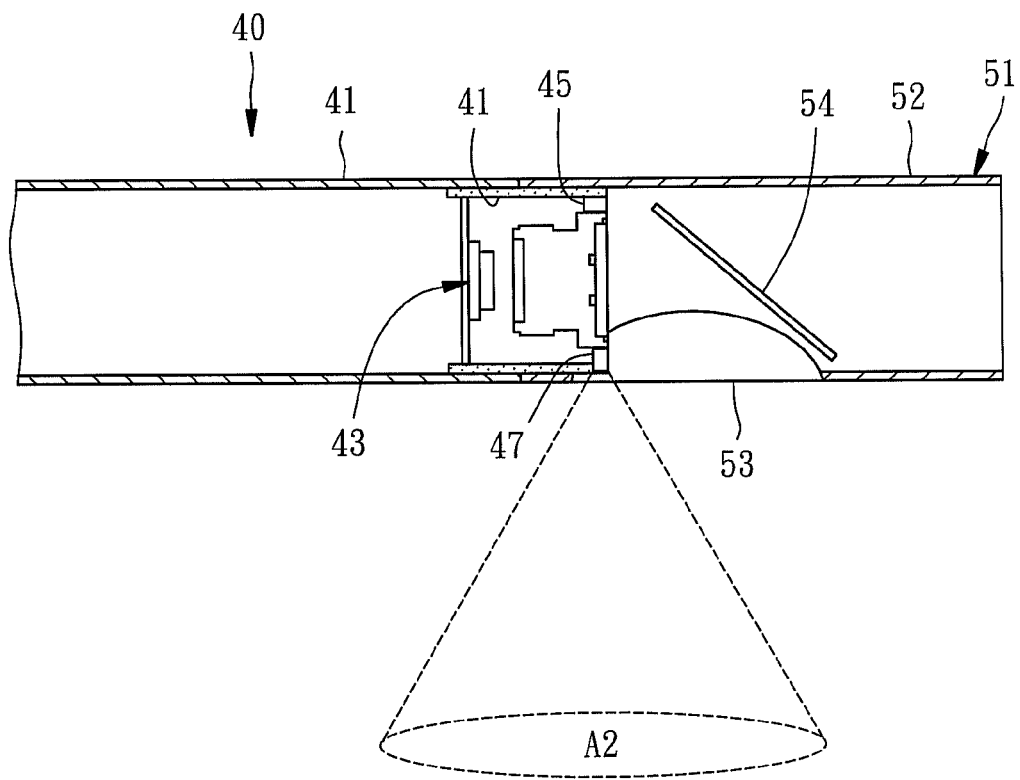
FIG. 5 is a schematic sectional view of an endoscopic image pickup device in accordance with a fourth embodiment of the present invention.
Figure 6:
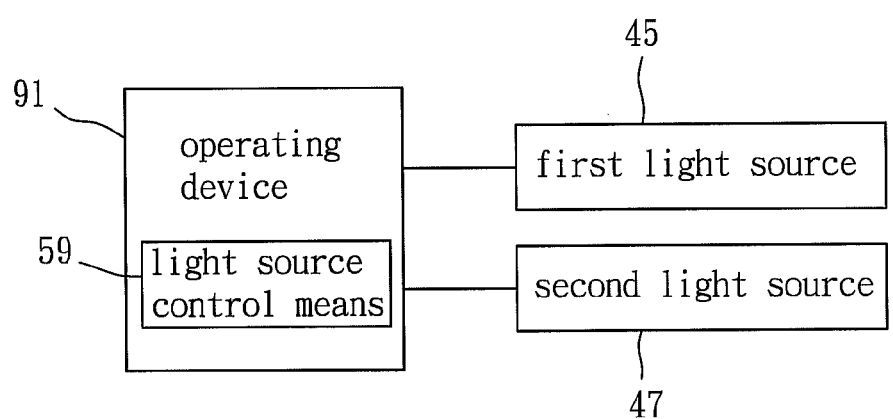
FIG. 6 is a system block diagram of the endoscopic image pickup device in accordance with the fourth embodiment of the present invention, illustrating the light source control means built in the operating device and electrically connected with the first light source and the second light source.

FIGS. 5 and 6 illustrate an endoscopic image pickup device 40 in accordance with a fourth embodiment of the present invention. This fourth embodiment is substantially similar to the aforesaid first embodiment with the exception that the first light source 45 consists of one single light-emitting component; the second light source 47 consists of one single light-emitting component; the illumination direction of the second light source 47 extends sideways relative to the tubing 41 and is deviated from the illumination direction of the first light source 45 at an angle of 90 degrees. However, it is to be understood that the design of single or multiple light-emitting components of the light sources is simply determined to match with the application but not intended for use as a limitation.

This fourth embodiment further comprises a side view attachment 51. The side view attachment 51 comprises a barrel 52 and a reflector 54. The barrel 52 is attached to the front end of the tubing 41 and kept in alignment with the image pickup module 43, having a transparent window 53 at one side thereof. The reflector 54 is mounted in the barrel 52 corresponding to the transparent window 53 and the image pickup module 43. The illumination range A2 of the second light source 47 corresponds to the transparent window 53. The light rays emitted by the second light source 47 and reflected by the target object enter the barrel 52 through the transparent window 53 and are then reflected by the reflector 54 onto the image pickup module 43 for image formation. Thus, the illumination range A2 of the second light source 47 is reflected by the target object and then intersected with the illumination range (not shown) of the first light source 45. FIG. 5 does not illustrates the status of intersection between reflection of the illumination range A2 of the second light source 47 and the illumination range of the first light source 45, however it can be assured, from the illumination of FIG. 5, that the light rays of the illumination range A2 of the second light source 47 after reflected by the target object can be intersected with the illumination range of the first light source 45.

As illustrated in FIG. 6, this fourth embodiment further comprises light source control means 59, for example, light source control unit, electrically connected with the first light source 45 and the second light source 47, and adapted for controlling on and/or off of the first light source 45 and/or the second light source 47. The light source control means 59 can be any conventional hardware circuit or control software for controlling on/off of light source means. According to this embodiment, the light source control means 59 is a control software built in the operating device 91 and electrically connected with the first light source 45 and the second light source 47, and operable by the user to selectively turn on/off the first light source 45 and the second light source 47. This design of soft ware light source control means 59 is of the known art commonly seen in conventional endoscopes, and therefore no further detailed description in this regard is necessary.

During operation of this fourth embodiment, as shown in FIG. 5, control the light source control means 59 to turn off the first light source 45 and simultaneously to turn on the second light source 47. At this time, the first light source 45 gives off no light, and the second light source 47 emits light laterally, and therefore no light is directly radiated onto the reflector 54. The light rays emitted by the second light source 47 and reflected by the target object (not shown) enter the barrel 52 through the transparent window 53, and is then reflected by the reflector 54 onto the image pickup module 43 for image formation.

Thus, it can be seen that, during operation of this fourth embodiment, the light rays emitted by the first light source 45 will not directly fall upon the reflector 54 of the side view attachment 51, and the reflector 54 simply reflects external incident light rays onto the image pickup module 43 for image formation, assuring high image clarity and avoiding picture quality interference due to lens surface contamination.

In other words, you can take advantage of greater fault tolerance for the coating quality and surface clearness of the reflector 54, lowering the manufacturing cost.

Figure 7:
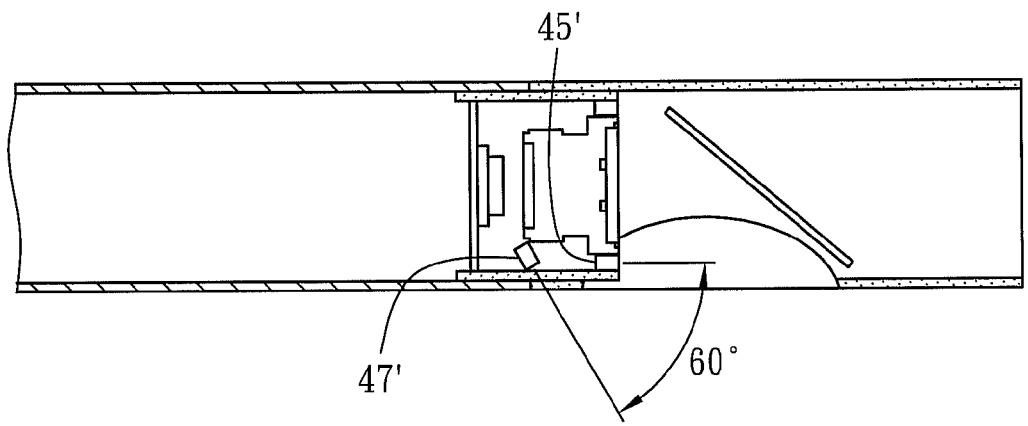
FIG. 7 is another schematic sectional view of the endoscopic image pickup device in accordance with the fourth embodiment of the present invention, illustrating the second light source shifted to a different angle.

Further, as illustrated in FIG. 7, there is a 60° difference in illumination direction between the second light source 47' and the first light source 45' in accordance with this fourth embodiment, i.e., the 90° deviation is not a limitation.

The other structural details and the effects of this fourth embodiment are substantially same as the aforesaid first embodiment. Therefore, no further detailed description in this regard is necessary.

In the aforesaid various embodiments, the light-emitting components of the first light source, the second light source and the third light source use LEDs (light-emitting diodes). In other examples of the present invention, the first light source, the second light source and the third light source can use fiber-optics. Using fiber-optics to make light source means is of the known art, no further detailed description in this regard is necessary.

In conclusion, the invention provides an endoscopic image pickup device, which has the advantages as follows:

1. In addition to the function of using the first light source to give off light for illumination and image pickup like the conventional illumination method, the invention provides an extra second light source to give an extra illumination range beyond the radiation direction of the first light source, enhancing image clarity.

2. The application of the fourth embodiment assures high image clarity and avoids picture quality interference due to lens surface contamination.

3. The fourth embodiment allows a greater fault tolerance for the coating quality and surface clearness of the reflector so that the manufacturing cost of the endoscopic image pickup device can be minimized.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. An endoscopic image pickup device, comprising:
a tubing;
an image pickup module comprising a lens and an image sensor, said image pickup module being installed in and fixed to one end of said tubing;
a first light source installed in said tubing at the same end relative to said image pickup module, said first light source having an illumination range directly intersected with the image pickup range of said image pickup module; and
a second light source installed in said tubing, said second light source having an illumination range deviated from the illumination range of said first light source at a predetermined angle and intersected with the illumination range of said first light source directly or indirectly;
a light source control means adapted for controlling whether said first light source and/or said second light source are on and/or off; and
a side view attachment, said side view attachment comprising a barrel and a reflector, said barrel being arranged to one end of said tubing adjacent to said image pickup module and having a transparent window at one lateral side thereof, said reflector being mounted inside said barrel and facing toward said transparent window and said image pickup module, the illumination range of said second light source corresponding to said transparent window so that external light rays entering said barrel through said transparent window are reflected by said reflector onto said image pickup module for image formation,
wherein an illumination direction of said second light source is deviated from an illumination direction of said first light source an angle of 90 degrees.

2. The endoscopic image pickup device as claimed in claim 1, wherein an illumination direction of said first light source is parallel to an image pickup direction of said image pickup module.

3. The endoscopic image pickup device as claimed in claim 1, wherein said light source control means is a light source control unit electrically connected with said first light source and said second light source and adapted for controlling on/off of said first light source and said second light source.

4. The endoscopic image pickup device as claimed in claim 1, further comprising a third light source, an illumination direction of said third light source being deviated from the illumination direction of said second light source a predetermined angle.

5. The endoscopic image pickup device as claimed in claim 4, wherein said first light source, said second light source and said third light source are selected from the group of light-emitting diodes and fiber-optics.

6. The endoscopic image pickup device as claimed in claim 4, wherein the illumination direction of said third light source is deviated from the illumination direction of said first light source a predetermined angle.

7. The endoscopic image pickup device as claimed in claim 1, wherein the end of said tubing carrying said image pickup module is the front end; said first light source is installed in the front end of said tubing; said second light source is installed in said tubing at a rear side relative to said first light source.

8. The endoscopic image pickup device as claimed in claim 1, wherein said first light source and said second light source have the same wavelength.

9. The endoscopic image pickup device as claimed in claim 1, wherein said first light source and said second light source have different wavelengths.

10. The endoscopic image pickup device as claimed in claim 1, wherein the side attachment is arranged to an end of the tubing where the first light source is installed.

* * * * *